United States Patent
Uchibori

(10) Patent No.: US 9,320,495 B2
(45) Date of Patent: Apr. 26, 2016

(54) ULTRASOUND PROBE AND ULTRASOUND DIAGNOSTIC IMAGING APPARATUS

(71) Applicant: KONICA MINOLTA, INC., Chiyoda-ku, Tokyo (JP)

(72) Inventor: Masami Uchibori, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 126 days.

(21) Appl. No.: 14/218,628

(22) Filed: Mar. 18, 2014

(65) Prior Publication Data

US 2014/0288430 A1    Sep. 25, 2014

(30) Foreign Application Priority Data

Mar. 19, 2013  (JP) ................................. 2013-056401

(51) Int. Cl.
*A61B 8/00* (2006.01)
*A61B 8/14* (2006.01)
*B06B 1/06* (2006.01)

(52) U.S. Cl.
CPC ................. *A61B 8/4444* (2013.01); *A61B 8/14* (2013.01); *A61B 8/4494* (2013.01); *B06B 1/0611* (2013.01); *B06B 1/0622* (2013.01)

(58) Field of Classification Search
CPC ...... A61B 8/14; A61B 8/4444; A61B 8/4494; B06B 1/0611; B06B 1/0622
See application file for complete search history.

(56) References Cited

U.S. PATENT DOCUMENTS

| 6,558,332 | B1* | 5/2003 | Shimizu | B06B 1/0622 600/437 |
| 2005/0187471 | A1* | 8/2005 | Kanayama | A61B 5/0091 600/437 |
| 2010/0198077 | A1* | 8/2010 | Ooura | A61B 8/08 600/459 |
| 2013/0245450 | A1* | 9/2013 | Prins | A61B 8/4494 600/459 |
| 2013/0281857 | A1* | 10/2013 | Ko | B06B 1/0629 600/443 |
| 2014/0204717 | A1* | 7/2014 | Kunkel | A61B 8/4272 367/137 |

FOREIGN PATENT DOCUMENTS

| JP | 51039700 A | 2/1986 |
| JP | 11056857 A | 3/1999 |
| JP | 11-276479 A | 10/1999 |

OTHER PUBLICATIONS

Japanese Office Action (and English translation thereof) dated Aug. 25, 2015, issued in counterpart Japanese Application No. 2013-056401.

* cited by examiner

*Primary Examiner* — Mark Remaly
(74) *Attorney, Agent, or Firm* — Holtz, Holtz & Volek PC

(57) ABSTRACT

An ultrasound probe includes a stack including a connecting conductor having conductive patterns and a piezoelectric plate disposed on the connecting conductor. The stack has first dividing slits at predetermined intervals. The first dividing slits divide the stack into transducers separate from one another and arrayed in the scanning direction. The conductive patterns are electrically connected to the transducers. Each of the transducers has a second dividing slit parallel to the first dividing slits. The second dividing slit divides each of the transducers into subelements. The first dividing slits extend through the connecting conductor. The second dividing slits are shallower than the first dividing slits and have bottoms apart from the connecting conductor.

9 Claims, 10 Drawing Sheets

→ SCANNING DIRECTION

ULTRASOUND PROBE AND ULTRASOUND DIAGNOSTIC IMAGING APPARATUS

BACKGROUND OF THE INVENTION

1. Field of the Invention

The present invention relates to an ultrasound probe and an ultrasound diagnostic imaging apparatus.

2. Description of Related Art

A typical ultrasound diagnostic imaging apparatus scans the interior of a subject with ultrasound waves and creates an image showing the interior on the basis of reception signals generated in response to the reflected ultrasound waves from the subject.

The ultrasound diagnostic imaging apparatus has an ultrasound probe emitting and receiving ultrasound waves to and from the subject.

With reference to FIG. 11, the ultrasound probe includes a plurality of transducers 200 arrayed in the scanning direction, for example. The transducers 200 are formed by bonding a piezoelectric layer (plate) 71, which includes two electrodes having opposite polarities, to a backing layer 73, which reflects, attenuates, and absorbs ultrasound waves directed backward, via a connecting conductor 72, which has conductive patterns 72a arrayed at predetermined intervals in the scanning direction, with an adhesive; and forming slits (primary slits) 74 in the bonded stack at predetermined intervals in such a way that the stack is divided into rectangular plates. The primary slits 74 extend from the piezoelectric plate 71 to the upper portion of the backing layer 73. The primary slits 74 each coincide with the gap between two adjacent conductive patterns 72a.

Each of the transducers 200 has a slit (secondary slit) 75 having a depth substantially identical to that of the primary slits 74 to define minute elements (subelements) 201 to improve their oscillation efficiency. The secondary slits 75 extend through the conductive patterns 72a.

Unfortunately, such strip subelements 201 may tilt by the loads (indicated by reference signs T in FIG. 11) thereon during the forming process.

Japanese Unexamined Patent Application Publication No. H11-276479, for example, discloses a technique to prevent the subelements from tilting, focusing attention on the structural differences in the connecting conductor between the portions of the primary slits and the portions of the secondary slits.

In specific, in the technique disclosed in Japanese Unexamined Patent Application Publication No. H11-276479, the connecting conductor has elongated openings at positions corresponding to the secondary slits so that the portions around the primary slits and the portions around the secondary slits in the connecting conductor are composed of the same material and have the same structure. This structure equalizes mechanical loads on the individual transducers (subelements) during the formation of the secondary slits to those during the formation of the primary slits, preventing the subelements from tilting.

Unfortunately, the technique disclosed in Japanese Unexamined Patent Application Publication No. H11-276479 cannot completely solve the problem of tilted subelements: thinner subelements still may tilt under some conditions during the forming process, for example.

In the technique disclosed in Japanese Unexamined Patent Application Publication No. H11-276479, the adhesive protrudes outside the openings of the conductive patterns on the connecting conductor, which impairs the workability in the processes after the bonding process.

SUMMARY OF THE INVENTION

The present invention has been made in view of the problems and aims to provide an ultrasound probe and an ultrasound diagnostic imaging apparatus that can prevent the subelements from tilting with satisfactory workability in the production.

In order to achieve the above object, an ultrasound probe reflecting one aspect of the present invention includes a stack including: a connecting conductor having conductive patterns; and a piezoelectric plate disposed on the connecting conductor, wherein the stack has first dividing slits at predetermined intervals, the first dividing slits dividing the stack into transducers separate from one another and arrayed in a scanning direction; the conductive patterns are electrically connected to the transducers; each of the transducers has a second dividing slit parallel to the first dividing slits, the second dividing slit dividing each of the transducers into subelements; the first dividing slits extend through the connecting conductor; and the second dividing slits are shallower than the first dividing slits and have bottoms apart from the connecting conductor.

Preferably, a ratio of a depth of the first dividing slits to a depth of the second dividing slits is higher than 1.0 and not higher than 1.2.

Preferably, a proportion of a depth of the second dividing slits to a thickness of the piezoelectric plate is not lower than 90% and lower than 100%.

An ultrasound probe reflecting another aspect of the present invention includes a stack including: a piezoelectric plate; a back reflecting layer disposed on a back surface of the piezoelectric plate; and a connecting conductor having conductive patterns, wherein the stack has first dividing slits at predetermined intervals, the first dividing slits dividing the stack into transducers separate from one another and arrayed in a scanning direction; the conductive patterns are electrically connected to the transducers; each of the transducers has a second dividing slit parallel to the first dividing slits, the second dividing slit dividing each of the transducers into subelements; the first dividing slits extend through the connecting conductor; and the second dividing slits are shallower than the first dividing slits and have bottoms apart from the connecting conductor.

Preferably, the bottoms of the second dividing slits are located above an interface between the piezoelectric plate and the back reflecting layer.

Preferably, a ratio of a depth of the first dividing slits to a depth of the second dividing slits is higher than 1.0 and not higher than 2.2.

Preferably, the bottoms of the second dividing slits are located below a center in a thickness direction of the back reflecting layer.

An ultrasound diagnostic imaging apparatus reflecting another aspect of the present invention includes the ultrasound probe emitting ultrasound waves to a subject in response to a drive signal and receiving ultrasound waves reflected by the subject to output a reception signal; and an image generation unit that generates ultrasound image data based on the reception signal outputted from the ultrasound probe.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein.

DESCRIPTION OF THE PREFERRED EMBODIMENTS

First Embodiment

An ultrasound diagnostic imaging apparatus according to embodiments of the present invention will now be described with reference to the drawings. The invention should not be limited to the illustrated examples.

[Ultrasound Diagnostic Imaging Apparatus]

Figure 1:
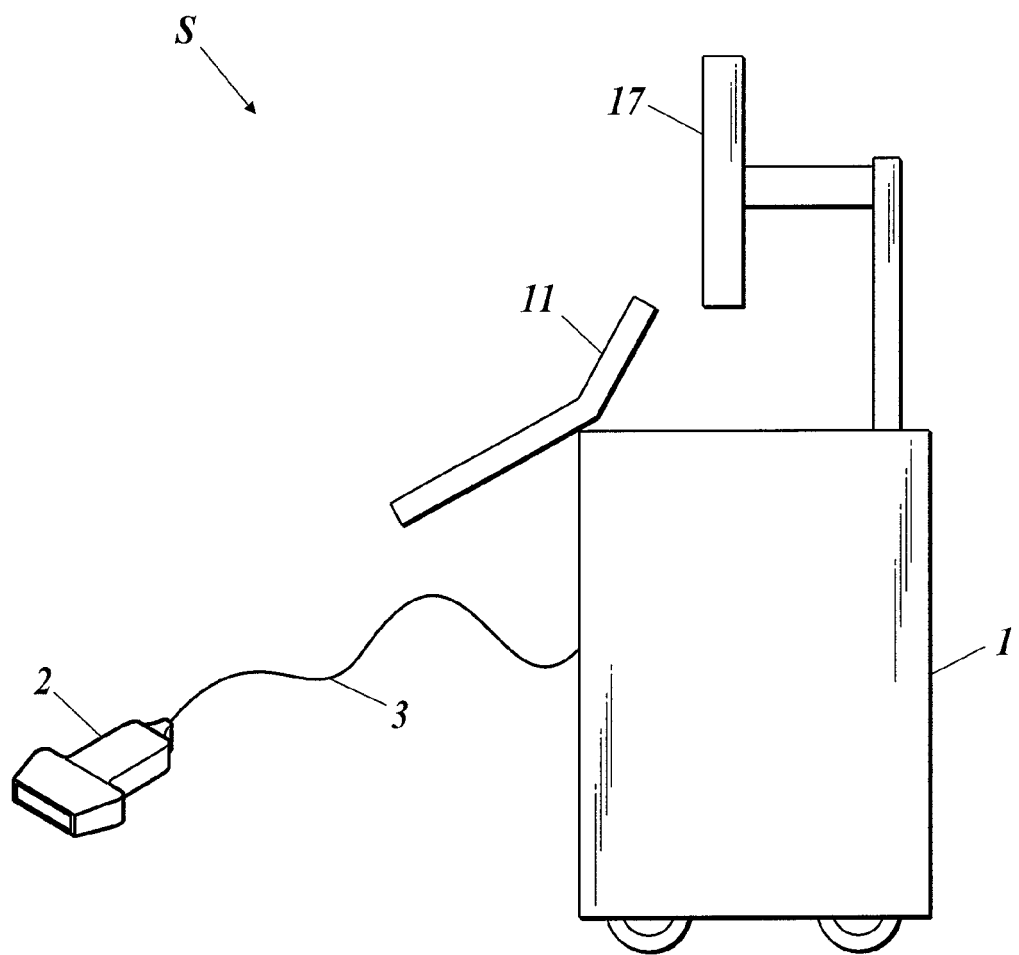
FIG. 1 is a schematic view of an ultrasound diagnostic imaging apparatus.
Figure 2:
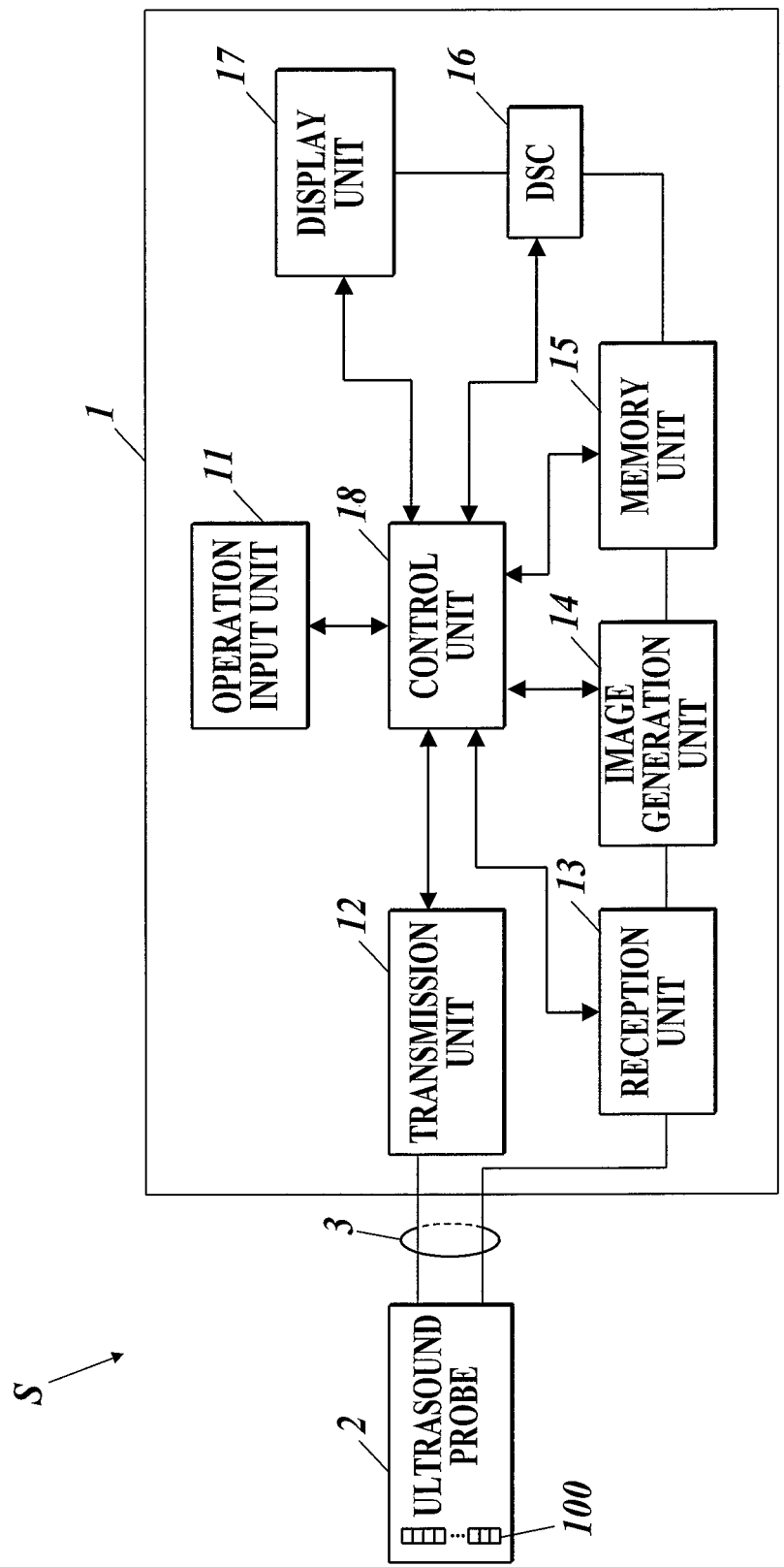
FIG. 2 is a block diagram illustrating the control configuration of an ultrasound diagnostic imaging apparatus.

With reference to FIGS. 1 and 2, an ultrasound diagnostic imaging apparatus S according to the present embodiment includes a body 1 and an ultrasound probe 2.

The body 1 is connected to the ultrasound probe 2 with a cable 3. The body 1 supplies the ultrasound probe 2 with electric drive signals to cause the ultrasound probe 2 to emit ultrasound waves to a subject such as a living body (not shown), and creates an ultrasound image showing the interior of the subject on the basis of electric reception signals generated in the ultrasound probe 2 in response to reflected ultrasound waves (echoes) from the subject received by the ultrasound probe 2.

The ultrasound probe 2 emits ultrasound waves to the subject and receives the ultrasound waves reflected by the subject.

The ultrasound probe 2 includes ultrasound transducers (hereinafter referred to as "transducers") 100, for example, which are constituted of piezoelectric elements disposed in a one-dimensional array in the orientation direction (scanning direction) (refer to FIG. 3). The ultrasound probe 2 includes any number of transducers 100 (e.g., 192 transducers 100 in the embodiment).

Although the ultrasound probe 2 in the embodiment is an electronic probe of a linear scanning type, the ultrasound probe 2 may be any of a mechanical scanning probe and an electronic scanning probe of a linear scanning, sector scanning, or convex scanning type. The bandwidth in the ultrasound probe 2 may be appropriately determined.

[Body of Ultrasound Diagnostic Imaging Apparatus]

With reference to FIG. 2, the body 1 includes an operation input unit 11, a transmission unit 12, a reception unit 13, an image generation unit 14, a memory unit 15, a digital scan converter (DSC) 16, a display unit 17, and a control unit 18, for example.

The operation input unit 11 includes operational components, such as various switches, buttons, a trackball, a mouse, and a keyboard, for inputting commands to start diagnosis and data such as personal information on the subject, for example. The operation input unit 11 outputs operation signals to the control unit 18.

The transmission unit 12 is a circuit that supplies the ultrasound probe 2 with electric drive signals through the cable 3 and causes the ultrasound probe 2 to generate ultrasound waves to be emitted, under the control of the control unit 18. The transmission unit 12 includes a clock circuit, a delay circuit, and a pulse generating circuit, for example.

The clock circuit generates clock signals for determining the transmission timing and frequency of drive signals.

The delay circuit determines a delay time for the path corresponding to each transducer 100 and delays the transmission of drive signals by the determined delay time, for focusing transmission beams of emitted ultrasound waves (transmission beam forming) and determining (steering) the angle of the transmission beams.

The pulse generating circuit generates pulsed drive signals in predetermined cycles.

The transmission unit 12 having such a structure, for example, drives continuous ones (e.g., 64 transducers) of the transducers 100 (e.g., 192 transducers) arrayed in the ultrasound probe 2 to generate ultrasound waves to be emitted, under the control of the control unit 18. The transmission unit 12 performs scanning by shifting transducers 100 to be driven in the orientation direction every generation of ultrasound waves to be emitted. The transmission unit 12 performs scanning while changing the angle of transmission beams and can scan with ultrasound waves over areas at different angles.

The reception unit 13 is a circuit that receives electric reception signals through the cable 3 from the ultrasound probe 2 under the control of the control unit 18. The reception unit 13 includes an amplifier, an analog-digital conversion circuit, and a phasing addition circuit, for example.

The amplifier is a circuit to amplify the reception signals by a predetermined gain for the path corresponding to each transducer 100.

The analog-digital conversion circuit converts the analog amplified reception signals into digital signals.

The phasing addition circuit gives delay times for the individual paths corresponding to the respective transducers 100 to the digital reception signals to phase the signals, and adds up the phased reception signals together to generate sound ray data.

The image generation unit 14 carries out processes such as envelope detection and logarithmic amplification to the sound ray data from the reception unit 13, and adjusts the gain for the luminance conversion to create B-mode image data. In other words, the B-mode image data indicates the intensities of reception signals in the form of luminance. The B-mode image data is transmitted from the image generation unit 14 to the memory unit 15.

The memory unit 15 includes a semiconductor memory such as a dynamic random access memory (DRAM), and stores the B-mode image data transmitted from the image generation unit 14 in frame units. In other words, the memory unit 15 can store diagnostic ultrasound image data constituted of frame units. The diagnostic ultrasound image data is read from the memory unit 15 and transmitted to the DSC 16 under the control of the control unit 18.

The DSC 16 converts the diagnostic ultrasound image data received from the memory unit 15 into image signals based on the scanning scheme for television signals, and outputs the converted image signals to the display unit 17.

Examples of the display unit 17 include a liquid crystal display (LCD), a cathode-ray tube (CRT) display, an organic electroluminescent (EL) display, an inorganic EL display, and a plasma display. The display unit 17 displays a diagnostic ultrasound image on its screen in response to the image signals output from the DSC 16. The display unit 17 may be replaced by any suitable component such as a printer.

The control unit 18 includes a central processing unit (CPU), a read only memory (ROM), and a random access memory (RAM), for example. The control unit 18 reads various processing programs such as a system program from the ROM to be expanded in the RAM, and performs centralized control of the operations of the individual components in the ultrasound diagnostic imaging apparatus S under the instructions of the expanded program.

The ROM includes a nonvolatile memory such as a semiconductor memory. The ROM stores a system program for the ultrasound diagnostic imaging apparatus S, various processing programs executable under the system program, and various pieces of data. These programs are stored in the form of computer-readable program codes, and the CPU sequentially executes operations under the instructions corresponding to the program codes.

The RAM defines a work area for temporarily storing various programs to be executed by the CPU and data related to the programs.

[Ultrasound Probe]

The structure of the ultrasound probe 2 according to the embodiment will now be described with reference to FIGS. 3 and 4.

Figure 3:
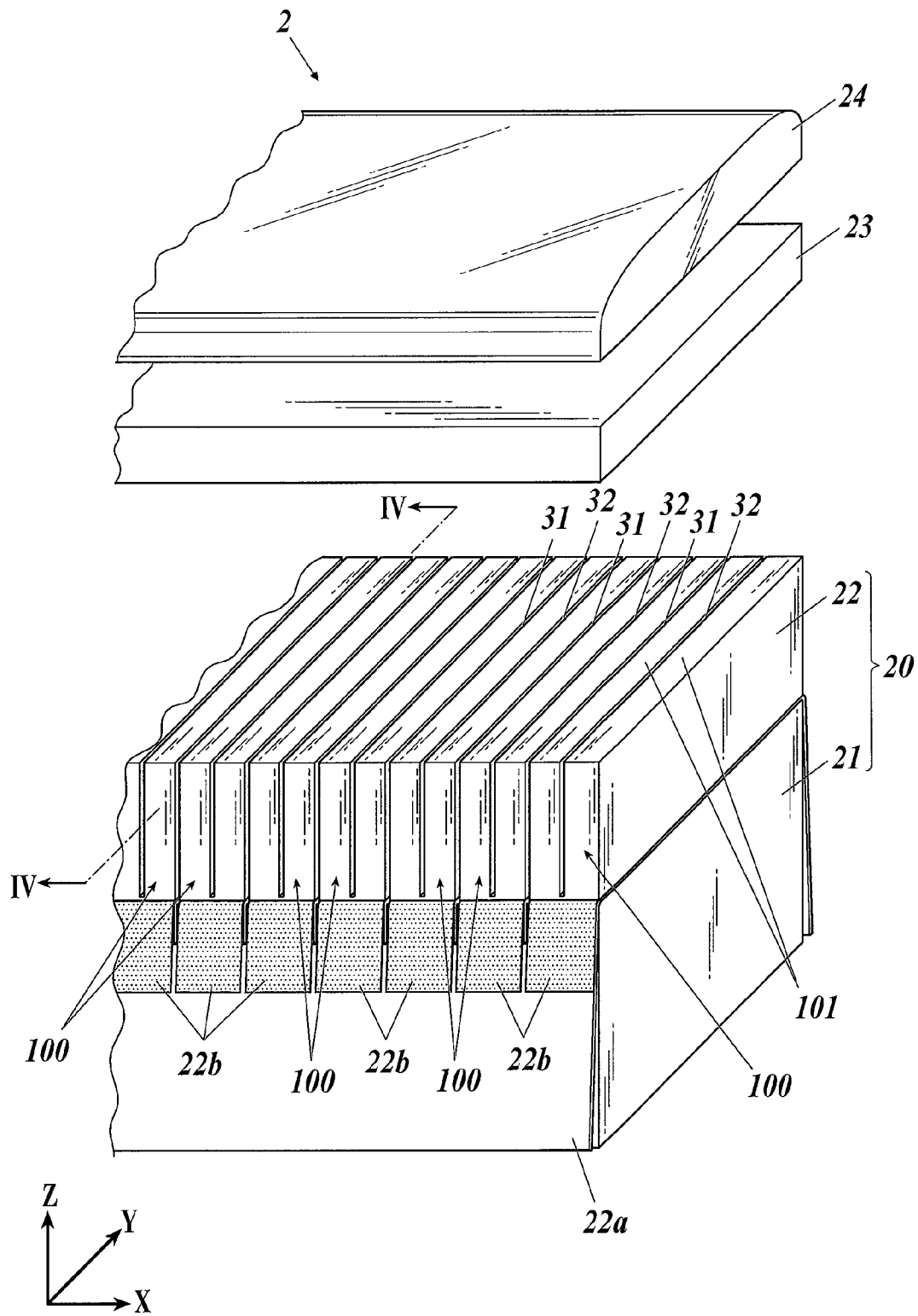
FIG. 3 is a schematic perspective view of an ultrasound probe according to a first embodiment.
Figure 4:
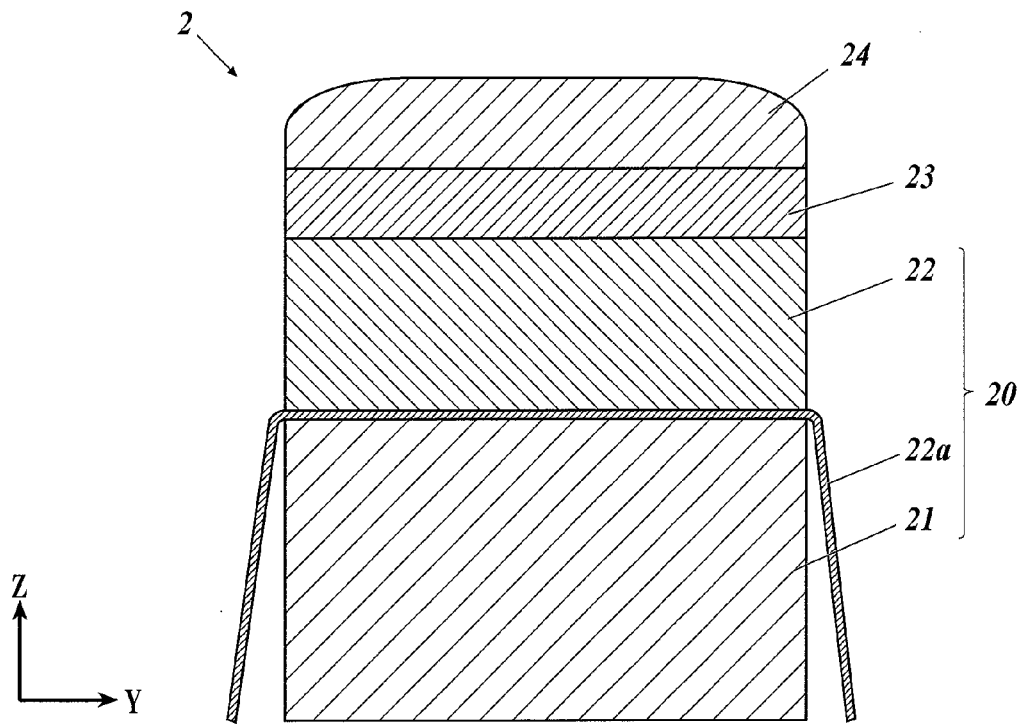
FIG. 4 is a cross-sectional view along the line IV-IV in FIG. 3.

FIG. 3 is an exploded schematic perspective view of the ultrasound probe 2, and FIG. 4 is a cross-sectional view along the line IV-IV in FIG. 3.

In FIG. 4, a stack 20, an acoustic matching layer 23, and an acoustic lens 24 (which are described below) are bonded together.

In the following description, the orientation direction (scanning direction) of the ultrasound probe 2 is defined as the X direction, the thickness direction of the transducers 100 as the Z direction, and the direction orthogonal to the X and Z directions as the Y direction.

With reference to FIGS. 3 and 4, the ultrasound probe 2 includes the stack 20 including a backing layer 21 and a piezoelectric layer 22 with a connecting conductor 22*a* therebetween, the acoustic matching layer 23 disposed on the piezoelectric layer 22, and the acoustic lens 24 disposed on the acoustic matching layer 23, for example.

The backing layer 21 supports the piezoelectric layer 22, and can absorb unnecessary ultrasound waves. In specific, the backing layer 21 is disposed on the surface, opposite to the surface through which ultrasound waves are emitted and received to and from a subject, of the piezoelectric layer 22; and absorbs ultrasound waves emitted in the direction opposite to the subject.

Examples of a backing material for the backing layer 21 include natural rubbers; ferrite rubber; epoxy resins; pressed rubber composites and epoxy-resin composites composed of the rubbers and resins containing powdered tungsten oxide, titanium oxide, or ferrite; and thermoplastic resins, such as vinyl chloride, polyvinyl butyral (PVB), ABS resins, polyurethanes (PUR), polyvinyl alcohol (PVAL), polyethylene (PE), polypropylene (PP), polyacetal (POM), polyethylene terephthalate (PETP), polytetrafluoroethylene (PTFE), polyethylene glycol, and copolymers of polyethylene terephthalate with polyethylene glycol.

Preferred backing materials among them are rubber composites and/or epoxy-resin composites. The backing material may have any shape depending on the shape of the upper ultrasound probe 2 or the piezoelectric layer 22 therein.

The piezoelectric layer 22 is a piezoelectric element that includes electrodes and a piezoelectric material, can convert electric signals into mechanical vibrations and convert mechanical vibrations into electric signals, and can emit and receive ultrasound waves.

The piezoelectric material can convert electric signals into mechanical vibrations and convert mechanical vibrations into electric signals. Examples of the piezoelectric material include lead zirconate titanate (PZT) ceramics; piezoelectric ceramics such as lead titanate and lead metaniobate; lithium niobate; piezoelectric single crystals of solid solutions (e.g., lead zinc niobate and lead titanate, and lead magnesium niobate and lead titanate); quartz crystal; Rochelle salt; and organic polymers, such as PVDF copolymers (e.g., poly(vinylidene fluoride-co-trifluoroethylene) (P(VDF-TrFE)), which are copolymers of polyvinylidene fluoride (PVDF) or VDF with trifluoroethylene (TrFE)), polyvinylidene cyanide (PVDCN, which is a polymer of vinylidene cyanide (VDCN)), vinylidene cyanide copolymers, odd nylons (e.g., nylon 9 and nylon 11), aromatic nylons, alicyclic nylons, polyhydroxycarboxylic acids (e.g., polylactate and polyhydroxybutyrate), cellulose derivatives, and polyureas.

The piezoelectric material has a thickness of approximately 100 to 500 µm. The piezoelectric material is provided with electrodes on its both surfaces to be used as transducers 100 (described below).

The electrodes provided to the piezoelectric material are made of metals, such as gold (Au), platinum (Pt), silver (Ag), palladium (Pd), copper (Cu), aluminum (Al), nickel (Ni), and tin (Sn).

The electrodes maybe formed on the piezoelectric material by a technique involving forming an underlying metal, such as titanium (Ti) or chromium (Cr), by spattering into a thickness of 0.02 to 1.0 µm; and forming a metallic material containing a metal composed mainly of the above-mentioned metallic element and its alloys, and partly forming an insulating material, as required, into a thickness of 1 to 10 µm by an appropriate process, such as spattering, for example.

The electrodes maybe formed by screen printing, dipping, or spraying, using a conductive paste containing a mixture of fine metal powder and low-melting-point glass, besides the spattering process. The electrodes are provided to the piezoelectric material on its entire or partial surfaces depending on the shape of the ultrasound probe 2.

The piezoelectric layer 22 is bonded to the connecting conductor 22*a* by a technique such as soldering, burning, or bonding. The electrodes of the piezoelectric layer 22 are in contact with the connecting conductor 22*a*. The connecting conductor 22*a*, which is electrically coupled with the cable 3, allows the drive signals from the body 1 to be inputted to the piezoelectric layer 22 and allows the reception signals from the piezoelectric layer 22 to be outputted to the body 1.

The connecting conductor 22*a* includes a substrate made of an insulator such as polyimide and conductive patterns 22*b*, which are made of copper for example, arrayed on the substrate at the same intervals as those of the transducers 100. Adjacent conductive patterns 22*b* are electrically insulated.

The gap between two adjacent conductive patterns 22b is substantially identical to the width of primary slits 31 (described below).

The piezoelectric layer 22 bonded with the connecting conductor 22a is disposed over the backing layer 21 preferably via an adhesive layer. The adhesive layer may be composed of an epoxy adhesive.

With reference to FIG. 3, the stack 20 has slits (first dividing slits; hereinafter referred to as "primary slits") 31 formed by dicing (i.e., processing with a dicing saw) at predetermined intervals, which define the transducers 100 (e.g., 192 transducers in the embodiment). The transducers 100 correspond to the respective conductive patterns 22b formed on the connecting conductor 22a.

In specific, the primary slits 31 extending from the piezoelectric layer 22 to a predetermined depth in the backing layer 21 are formed in the stack 20 at predetermined intervals in the X direction, with dicing blades arranged in the Y direction. This operation divides the piezoelectric layer 22, the substrate of the connecting conductor 22a, and the upper portion of the backing layer 21, and defines the transducers 100 in a one-dimensional array. The gap between the two adjacent transducers 100 defines the primary slit 31.

In general, the transducer 100 can most efficiently emit and receive ultrasound waves if the ratio w/t is approximately 0.6 where w is the width (i.e., dimension in the X direction) and t is the height (i.e., dimension in the Z direction) of the transducer 100.

The transducers 100 according to the embodiment each further have another slit (second dividing slit; hereinafter referred to as "secondary slit") 32 to improve the oscillation efficiency.

In specific, the piezoelectric layer 22 is diced to a predetermined depth with dicing blades arranged in the Y direction for the respective transducers 100, to define smaller elements (hereinafter referred to as "subelements") 101. The gap between the subelements of each transducer 100 defines the secondary slit 32.

The primary slits 31 extend through the substrate of the connecting conductor 22a, as described above.

The secondary slits 32 are shallower than the primary slits 31 and have bottoms located at a predetermined distance above the connecting conductor 22a. In other words, the secondary slits 32 have a depth smaller than that of the primary slits 31 and do not reach the connecting conductor 22a.

The ratio of the depth of the primary slits 31 to that of the secondary slits 32 is preferably higher than 1.0 and not higher than 1.2.

If the ratio of the depth of the primary slits 31 to that of the secondary slits 32 is higher than 1.0, the structure can prevent the subelements 101 from tilting by the action of mechanical loads thereon during the dicing process. At a ratio of not higher than 1.2, the structure can avoid the problem of a poor spectrum of the transmission band which would be caused by a large difference in depth between the primary slits 31 and the secondary slits 32.

The proportion of the depth of the secondary slits 32 to the thickness of the piezoelectric layer 22 is preferably not lower than 90% and lower than 100%.

If the proportion of the depth of the secondary slits 32 to the thickness of the piezoelectric layer 22 is not lower than 90% and lower than 100%, the undivided portions of the piezoelectric layer 22 between the bottoms of the secondary slits 32 and the connecting conductor 22a can have any appropriate vertical length. This structure can provide an excellent spectrum of the transmission band.

The acoustic matching layer 23 matches the acoustic impedances between the piezoelectric layer 22 and a subject and prevents the reflection on their interface. The acoustic matching layer 23 is disposed on the subject-side surface of the piezoelectric layer 22, through which ultrasound waves are emitted and received to and from the subject.

The acoustic matching layer 23 includes at least one sublayer and may include two or more sublayers.

The acoustic matching layer 23 preferably has a thickness of $\lambda/4$, where $\lambda$ indicates the wavelength of ultrasound waves. The acoustic matching layer 23 having an inappropriate thickness may lead to spurious emission at frequencies different from the proper resonance frequency, to significantly vary the basic acoustic characteristics. This variation may increase the reverberation time and distort the waveform of reflected echoes, leading to a decline in the sensitivity and the S/N ratio. A general acoustic matching layer has a thickness of approximately 20 to 500 μm.

The acoustic matching layer 23 has an acoustic impedance approximately intermediate between the piezoelectric layer 22 and a subject.

In the acoustic matching layer 23 including two or more sublayers, the acoustic impedance gradually decreases from the bottom sublayer to the top sublayer.

Examples of the material for the acoustic matching layer 23 include aluminum, aluminum alloys (e.g., Al—Mg alloy), magnesium alloys, Macor (R), glass, fused quartz, copper graphite, polyethylene (PE), polypropylene (PP), polycarbonates (PC), ABC resins, ABS resins, AAS resins, AES resins, polyamides (6-nylon and 6,6-nylon), polyphenylene oxide (PPO), polyphenylene sulfide (PPS; which may contain glass fibers), polyphenylene ether (PPE), polyether ether ketones (PEEKs), polyamide imides (PAIs), polyethylene terephthalate (PETP), epoxy resins, and urethane resins. Preferred materials are molded thermosetting resins, such as epoxy resins, containing a filler, such as zinc oxide, titanium oxide, silica, aluminum oxide, red iron oxide, ferrite, tungsten oxide, ytterbium oxide, barium sulfate, tungsten, or molybdenum.

In the embodiment, the material preferably at least contains silicone resin particles.

The acoustic lens 24 is disposed on the acoustic matching layer 23 to focus ultrasound beams by means of refraction and improve the resolution. In specific, the acoustic lens 24 is provided in the ultrasound probe 2 to come into contact with a subject, and efficiently emits the ultrasound waves generated in the piezoelectric layer 22 to the subject. The acoustic lens 24, which is to come into contact with the subject, is a convex or concave lens depending on the ultrasound velocity therein, and converges the ultrasound waves to be emitted to the subject in the thickness direction (elevation direction) orthogonal to a cross section to be imaged.

The acoustic lens 24 is made of a flexible polymer material having an acoustic impedance approximately intermediate between the acoustic matching layer 23 and the subject.

Examples of the material for the acoustic lens 24 include known homopolymer rubbers, such as silicone rubber, butadiene rubber, polyurethane rubber, and epichlorohydrin rubber; and copolymer rubbers, such as ethylene-propylene copolymer rubber, which is a copolymer of ethylene with propylene. Preferred materials among them are silicone rubber and butadiene rubber.

The operations of the ultrasound probe 2 according to the embodiment will now be explained.

In the ultrasound probe 2 according to the embodiment, the primary slits 31 extend through the substrate of the connecting conductor 22a, while the secondary slits 32 are shallower than the primary slits 31 and have bottoms apart from the connecting conductor 22a.

The piezoelectric layer 22 accordingly has undivided portions between the bottoms of the secondary slits 32 in the respective transducers 100 and the connecting conductor 22a. This structure can stabilize the subelements 101, thereby preventing them from tilting.

Spectra of the transmission band of the ultrasound probe 2 according to the embodiment will now be described with reference to FIG. 5.

Figure 5:
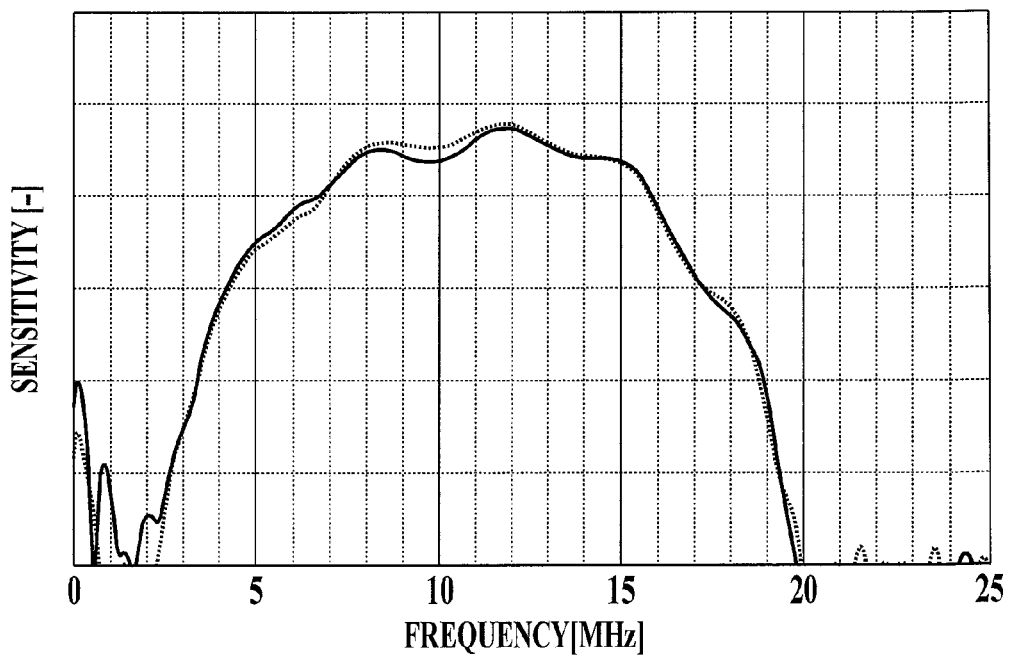
FIG. 5 is a spectrum diagram illustrating the transmission band of an ultrasound probe according to the first embodiment.

In FIG. 5, the vertical axis indicates the sensitivity [−] while the horizontal axis indicates the frequency [MHz].

The solid line in FIG. 5 indicates a spectrum of the transmission band of the ultrasound probe, in which the ratio of the depth of the primary slits 31 to that of the secondary slits 32 is 1.2. The dotted line in FIG. 5 indicates a spectrum of the transmission band of the ultrasound probe, in which the ratio is 1.05 and the proportion of the depth of the secondary slits 32 to the thickness of the piezoelectric layer 22 is 90%.

The ultrasound probe, in which the ratio of the depth of the primary slits 31 to that of the secondary slits 32 is 1.2, can provide an excellent spectrum of the transmission band having bilateral symmetry, as illustrated in FIG. 5.

The ultrasound probe, in which the ratio of the depth of the primary slits 31 to that of the secondary slits 32 is 1.05 and the proportion of the depth of the secondary slits 32 to the thickness of the piezoelectric layer 22 is 90%, can provide an excellent spectrum of the transmission band having better bilateral symmetry.

According to the embodiment, the ultrasound probe 2 includes a stack including a connecting conductor 22a having conductive patterns 22b, and a plate piezoelectric layer 22 disposed on the connecting conductor 22a. The stack has the primary slits 31 at predetermined intervals, which primary slits 31 divide the stack into transducers 100 separate from one another and arrayed in the scanning direction. The conductive patterns 22b are electrically connected to the transducers 100. Each of the transducers 100 has the secondary slit 32 parallel to the primary slits 31, which secondary slit 32 divides each of the transducers 100 into subelements 101. The primary slits 31 extend through the connecting conductor 22a. The secondary slits 32 are shallower than the primary slits 31 and have bottoms apart from the connecting conductor 22a.

The piezoelectric layer 22 accordingly has undivided portions between the bottoms of the secondary slits 32 and the connecting conductor 22a. This structure can stabilize the subelements 101, thereby preventing them from tilting.

The prevention of the tilt of the subelements 101 ensures excellent acoustic characteristics.

According to the embodiment, the ratio of the depth of the primary slits 31 to that of the secondary slits 32 is higher than 1.0 and not higher than 1.2.

This structure can reduce asymmetric vibrations and achieve an ultrasound probe showing excellent acoustic characteristics.

According to the embodiment, the proportion of the depth of the secondary slits 32 to the thickness of the piezoelectric layer 22 is not lower than 90% and lower than 100%.

This structure can achieve the ultrasound probe showing more excellent acoustic characteristics.

Figure 6:
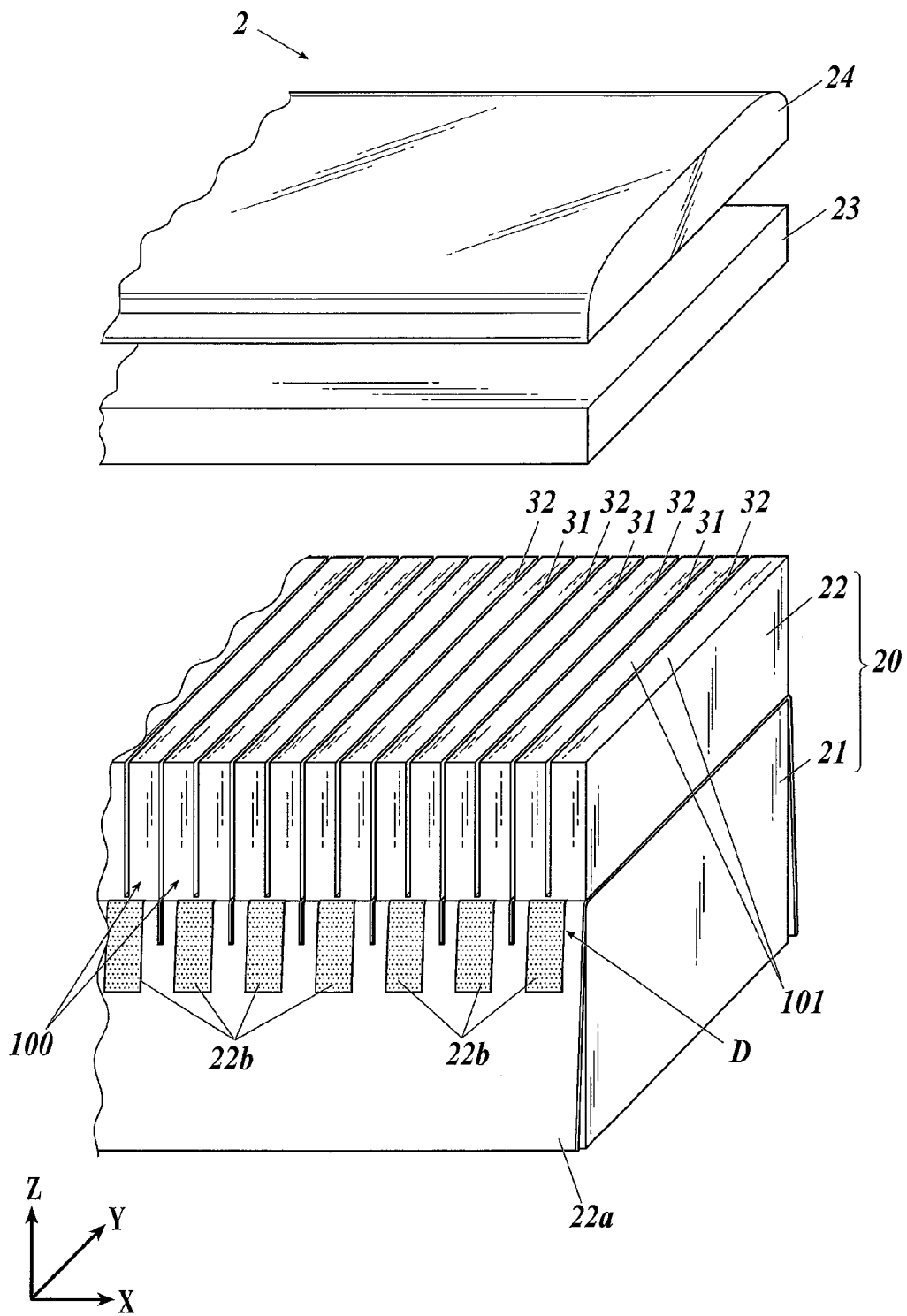
FIG. 6 illustrates a modified embodiment of the ultrasound probe in FIG. 3.

The conductive patterns 22b are provided over the substantially entire surface in the X direction of the connecting conductor 22a except the portions of the primary slits 31 in the embodiment illustrated in FIG. 3. Alternatively, each of the conductive patterns 22b on the connecting conductor 22a may be narrowed in the X direction, as illustrated in FIG. 6, for example. In this case, the conductive patterns 22b have steps D at their edges from the substrate. This structure more readily causes the tilt of the subelements for the conventional secondary slits having a depth substantially identical to that of the primary slits, if the positions of the secondary slits coincide with the positions of the steps D, for example.

In contrast, the piezoelectric layer 22 in the embodiment has undivided portions between the bottoms of the secondary slits 32 and the connecting conductor 22a, which prevent the subelements from tilting regardless of the shape (i.e., width in the X direction) of each conductive pattern 22b.

The stack 20, which includes the stacked piezoelectric layer 22, connecting conductor 22a, and backing layer 21, is diced in the embodiment illustrated in FIG. 3. The acoustic matching layer 23 disposed on the piezoelectric layer 22 may also be diced together with the stack 20.

For such slits extending from the acoustic matching layer 23, the thickness of the acoustic matching layer 23 is subtracted from the depth of each slit in calculating the ratio of the depth of the primary slits 31 to that of the secondary slits 32.

In other words, the ratio of the depth of the primary slits 31 to that of the secondary slits 32 is defined within the structure including the piezoelectric layer 22, the connecting conductor 22a, and the backing layer 21, even if the slits are provided through the acoustic matching layer 23 or not.

Second and third embodiments of the present invention will now be described.

In the second and third embodiments, ultrasound probes 2A and 2B each have a structure different from that in the first embodiment, while the body 1 has a structure identical to that in the first embodiment and will not be redundantly described.

In the following description, the components having functions and structures identical to those in the first embodiment will be referred to by the same reference signs without redundant description.

Second Embodiment

Figure 7:
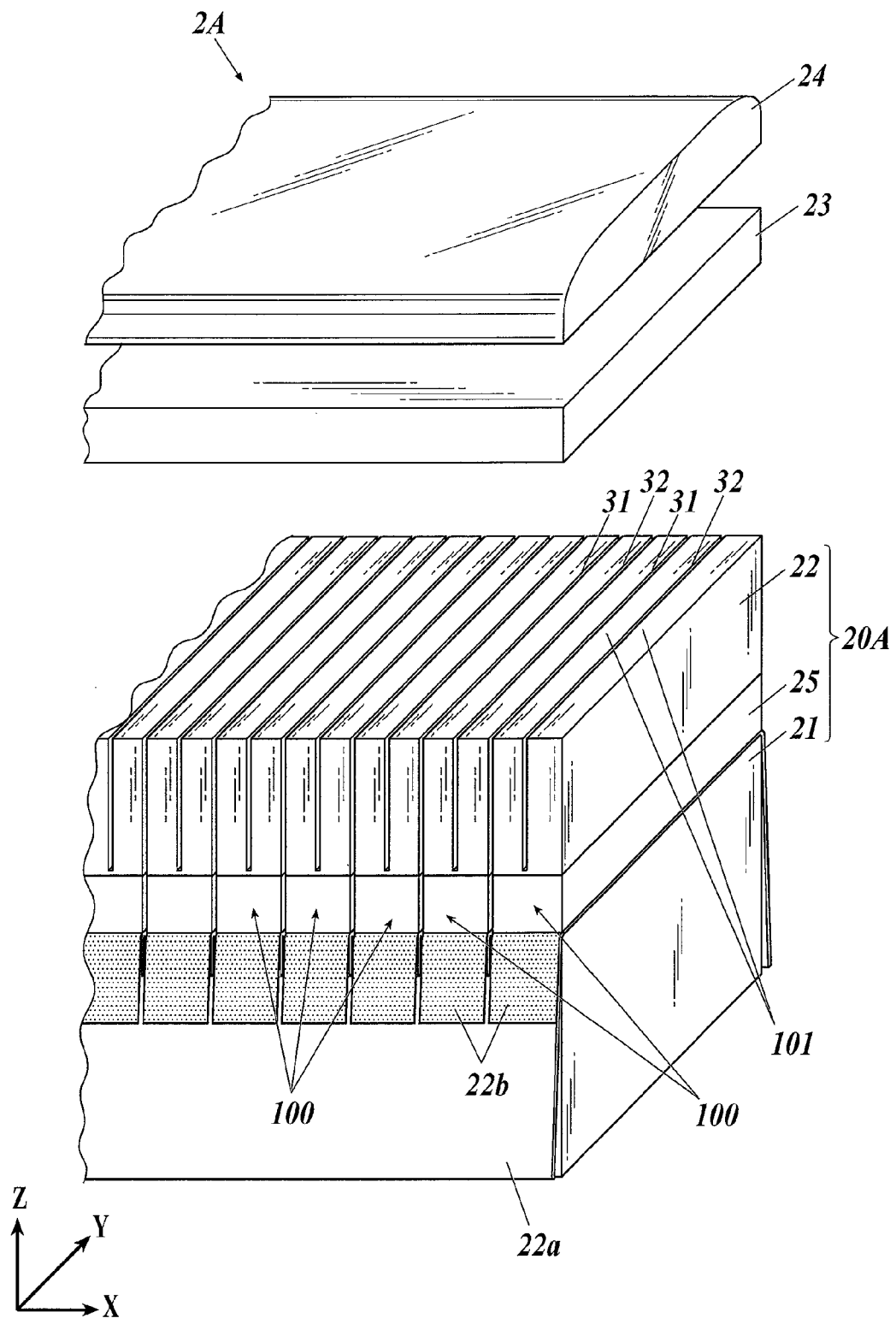
FIG. 7 is a schematic perspective view of an ultrasound probe according to a second embodiment.

FIG. 7 is a schematic perspective view of an ultrasound probe 2A according to the second embodiment.

With reference to FIG. 7, the ultrasound probe 2A includes a stack 20A including a backing layer 21, a connecting conductor 22a, a heavy backing layer 25, and a piezoelectric layer 22, which are stacked in sequence from the bottom to the top; an acoustic matching layer 23 disposed on the piezoelectric layer 22; and an acoustic lens 24 disposed on the acoustic matching layer 23, for example.

The heavy backing layer 25 is a back reflecting layer provided between the piezoelectric layer 22 and the backing layer 21.

The heavy backing layer 25 is composed of a material having an acoustic impedance higher than that of the piezoelectric layer 22, and reflects ultrasound waves outputted in the direction opposite to a subject with respect to the piezoelectric layer 22. The heavy backing layer 25 can further increase the sensitivity to emitted and received ultrasound waves of the piezoelectric layer 22. If the heavy backing layer 25 narrows the bandwidth, the acoustic matching layer 23 may have three or more sublayers to broaden the bandwidth.

In the ultrasound probe 2A according to the embodiment, primary slits 31 extend through the connecting conductor 22a.

Secondary slits 32 are shallower than the primary slits 31 and have bottoms located at a predetermined distance above the connecting conductor 22a. In specific, the secondary slits 32 do not reach the bottom of the piezoelectric layer 22, and the bottoms of the secondary slits 32 are located above the interface between the piezoelectric layer 22 and the heavy backing layer 25. In more specific, the proportion of the depth of the secondary slits 32 to the thickness of the piezoelectric layer 22 is preferably not lower than 90% and lower than 100%. At a proportion not lower than 90% and lower than 100%, the undivided portions of the piezoelectric layer 22 can have any appropriate vertical length. This structure can provide an excellent spectrum of the transmission band.

In this structure, the undivided portions of the piezoelectric layer 22 and the heavy backing layer 25 between the bottoms of the secondary slits 32 and the connecting conductor 22a can stabilize the subelements 101, thereby preventing them from tilting.

The prevention of the tilt of the subelements ensures excellent acoustic characteristics.

The dicing process does not completely divide the piezoelectric layer 22, and imposes smaller process loads.

A spectrum of the transmission band of the ultrasound probe 2A according to the embodiment will now be described with reference to FIG. 8.

Figure 8:
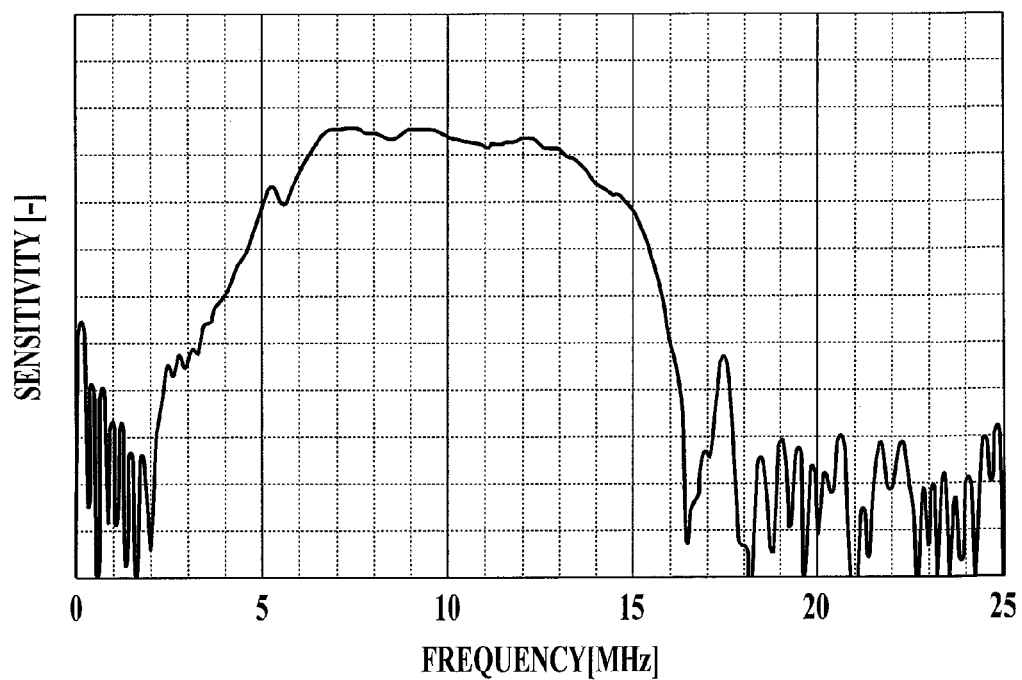
FIG. 8 is a spectrum diagram illustrating the transmission band of an ultrasound probe according to the second embodiment.

In FIG. 8, the vertical axis indicates the sensitivity [-] while the horizontal axis indicates the frequency [MHz].

FIG. 8 is a spectrum diagram illustrating the transmission band of the ultrasound probe 2A, in which the proportion of the depth of the secondary slits 32 to the thickness of the piezoelectric layer 22 is 90%.

With reference to FIG. 8, the ultrasound probe 2A can also provide an excellent spectrum of the transmission band having approximately bilateral symmetry.

Third Embodiment

Figure 9:
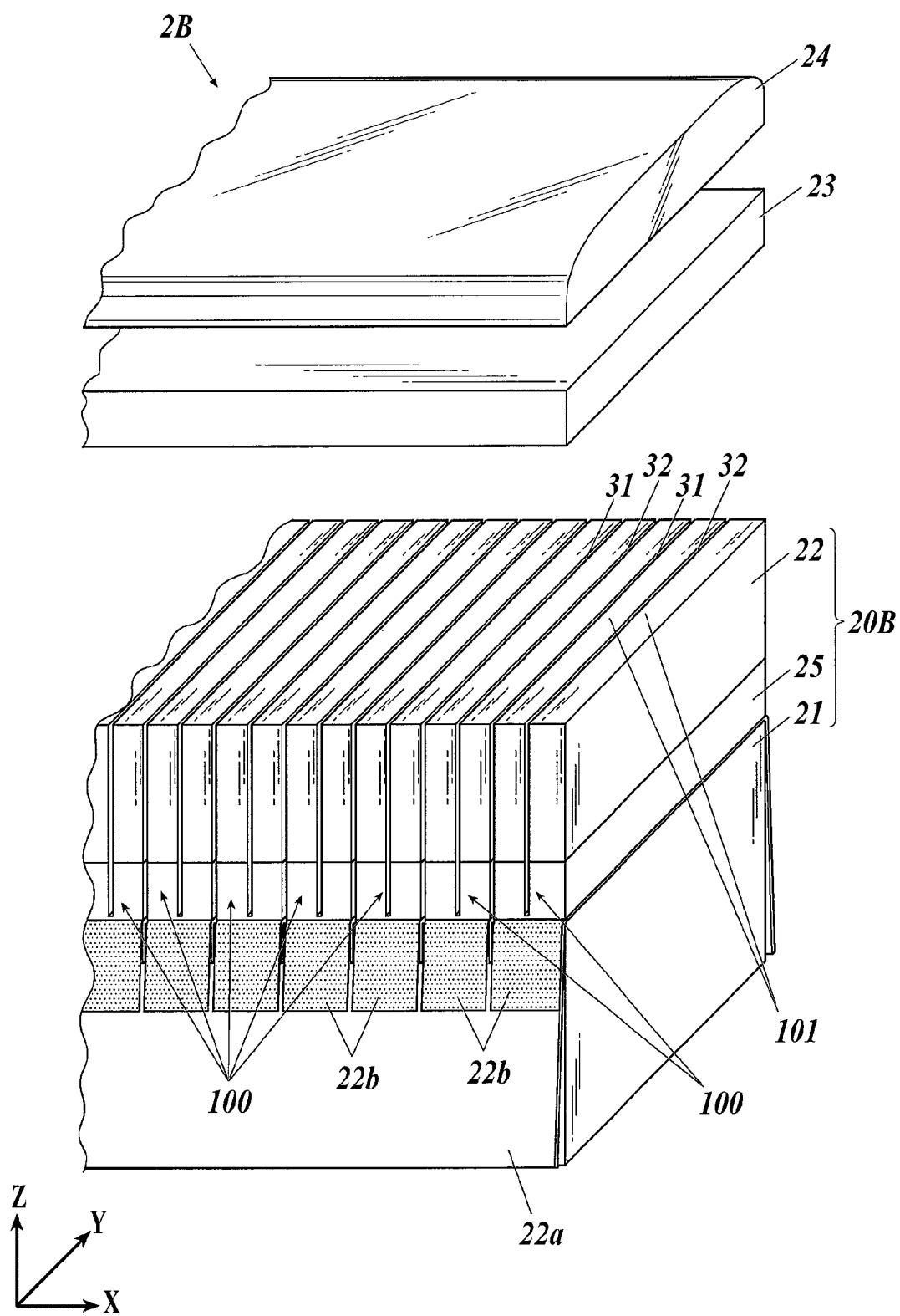
FIG. 9 is a schematic perspective view of an ultrasound probe according to a third embodiment.

FIG. 9 is a schematic perspective view of an ultrasound probe 2B according to the third embodiment.

With reference to FIG. 9, the ultrasound probe 2B includes a stack 20B including a backing layer 21, a connecting conductor 22a, a heavy backing layer 25, and a piezoelectric layer 22, which are stacked in sequence from the bottom to the top; an acoustic matching layer 23 disposed on the piezoelectric layer 22; and an acoustic lens 24 disposed on the acoustic matching layer 23, for example.

In the ultrasound probe 2B according to the embodiment, primary slits 31 extend through the connecting conductor 22a.

Secondary slits 32 are shallower than the primary slits 31 and have bottoms located at a predetermined distance above the connecting conductor 22a.

In specific, the secondary slits 32 extend to a predetermined depth below the center in the thickness direction of the heavy backing layer 25.

The ratio of the depth of the primary slits 31 to that of the secondary slits 32 is preferably higher than 1.0 and not higher than 2.2.

If the depth of the primary slits 31 to that of the secondary slits 32 is higher than 1.0, the structure can prevent the subelements 101 from tilting by the action of mechanical loads thereon during the dicing process. At a ratio of not higher than 2.2, the structure can avoid the problem of a poor spectrum of the transmission band which would be caused by a large difference in depth between the primary slits 31 and the secondary slits 32.

The bottoms of the secondary slits 32 are preferably located below the center in the thickness direction of the heavy backing layer 25.

If the bottoms of the secondary slits 32 are located below the center in the thickness direction of the heavy backing layer 25, the undivided portions of the heavy backing layer 25 between the bottoms of the secondary slits 32 and the connecting conductor 22a can have any appropriate vertical length. This structure can provide an excellent spectrum of the transmission band.

Spectra of the transmission band of the ultrasound probe 2B according to the embodiment will now be described with reference to FIG. 10.

Figure 10:
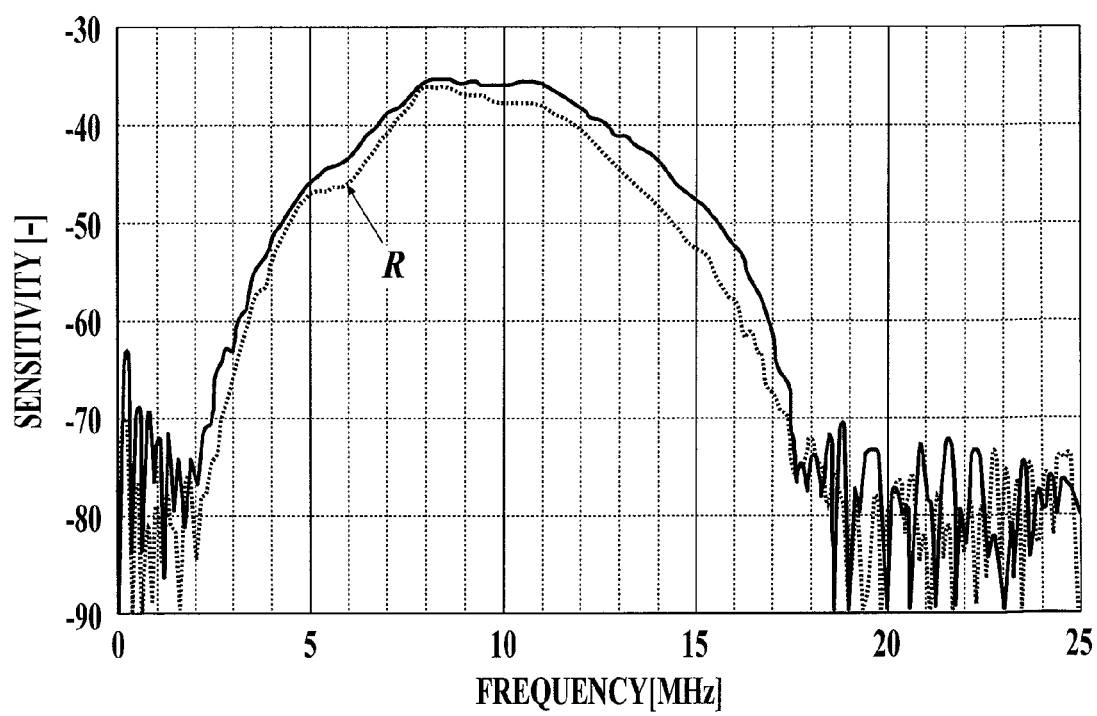
FIG. 10 a spectrum diagram illustrating the transmission band of an ultrasound probe according to the third embodiment.
Figure 11:
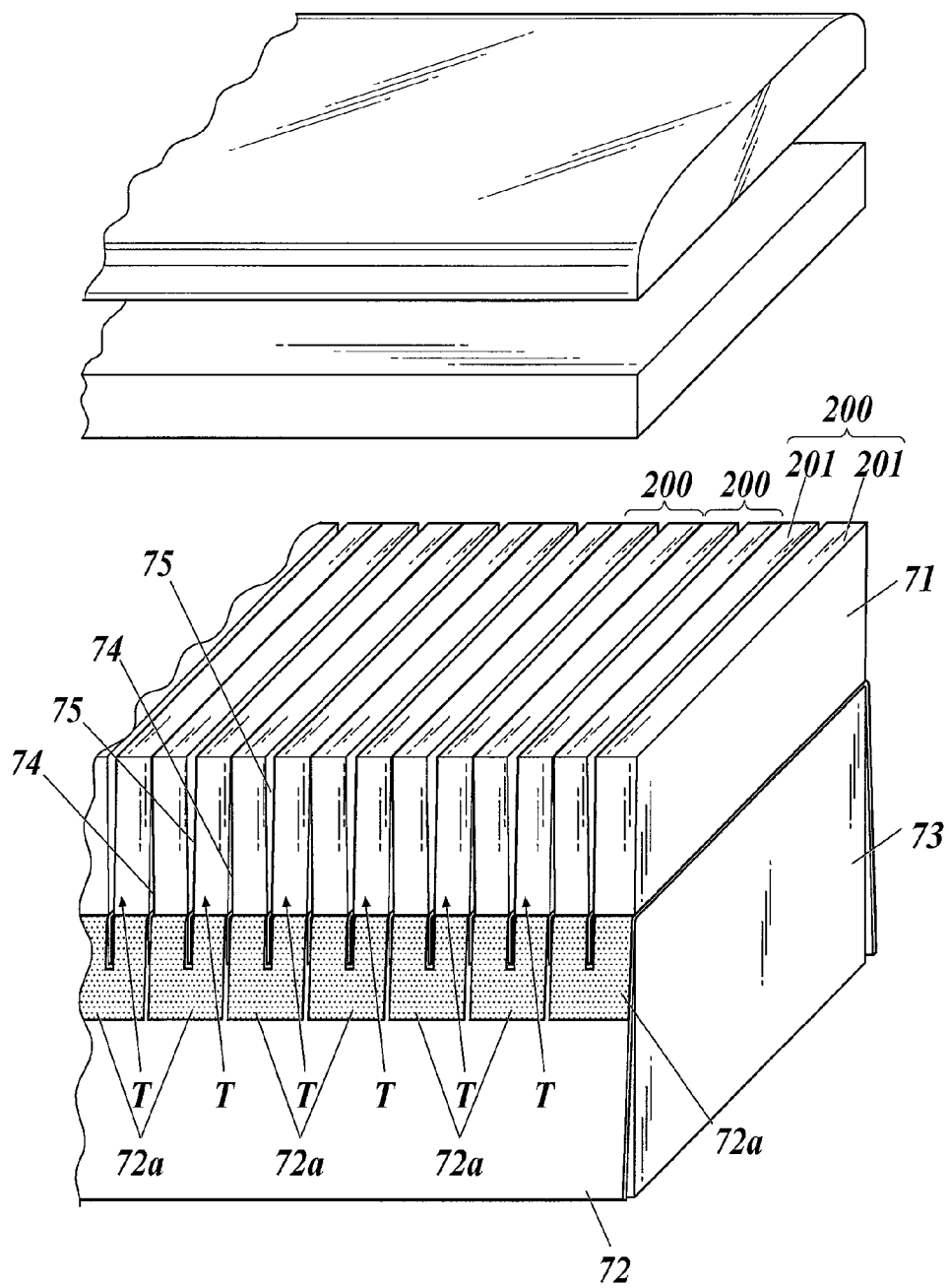
FIG. 11 illustrates a problem in a conventional ultrasound probe.

In FIG. 10, the vertical axis indicates the sensitivity [-] while the horizontal axis indicates the frequency [MHz].

In FIG. 10, the solid line indicates a spectrum of the transmission band of an ultrasound probe having a ratio of 2.2 of the depth of the primary slits 31 to that of the secondary slits 32; while the dotted line indicates a spectrum of the transmission band of an ultrasound probe having a ratio of 2.3.

With reference to FIG. 10, a ripple (indicated by reference sign R) appears in the band of the ultrasound probe having the ratio 2.3 of the depth of the primary slits 31 to that of the secondary slits 32.

In contrast, no ripple appears in the band of the ultrasound probe having the ratio 2.2 of the depth of the primary slits 31 to that of the secondary slits 32. This ultrasound probe can reduce asymmetric vibrations and shows excellent acoustic characteristics.

The ultrasound probe having the ratio 2.2 of the depth of the primary slits 31 to that of the secondary slits 32 shows frequency characteristics broader than those of the ultrasound probe having the ratio of 2.3.

In this structure, the heavy backing layer 25 has undivided portions between the bottoms of the secondary slits 32 and the connecting conductor 22a to stabilize the subelements 101, thereby preventing them from tilting.

The prevention of the tilt of the subelements ensures excellent acoustic characteristics.

The ratio of the depth of the primary slits 31 to that of the secondary slits 32 is adjusted to be higher than 1.0 and not higher than 2.2 so that the ultrasound probe can reduce asymmetric vibrations due to a difference in depth between the primary slits 31 and the secondary slits 32, showing excellent acoustic characteristics. The ratio also enables the ultrasound probe to show a sufficiently high time response, with no undue influence of the heavy backing layer 25.

The stack 20A or 20B, which includes the stacked piezoelectric layer 22, heavy backing layer 25, connecting conductor 22a, and backing layer 21, is diced in the second and third embodiments illustrated in FIGS. 7 and 9. The acoustic matching layer 23 disposed on the piezoelectriclayer 22 may also be diced together with the stack 20A or 20B.

For such slits extending from the acoustic matching layer 23, the thickness of the acoustic matching layer 23 is subtracted from the depth of each slit in calculating the ratio of the depth of the primary slits 31 to that of the secondary slits 32.

In other words, the ratio of the depth of the primary slits 31 to that of the secondary slits 32 is defined within the structure including the piezoelectric layer 22, the heavy backing layer 25, the connecting conductor 22a, and the backing layer 21, even if the slits are provided through the acoustic matching layer 23 or not.

The above-described details of the first to third embodiments may be appropriately modified without departing from the gist of the present invention.

Although the transducers 100 are disposed in a one-dimensional array in the X direction in the first to third embodiments, the transducers 100 may be disposed in a two-dimensional array, for example.

The entire disclosure of Japanese Patent Application No. 2013-056401 filed on Mar. 19, 2013 including description, claims, drawings, and abstract are incorporated herein by reference in its entirety.

Although various exemplary embodiments have been shown and described, the invention is not limited to the embodiments shown. Therefore, the scope of the invention is intended to be limited solely by the scope of the claims that follow.

What is claimed is:

1. An ultrasound probe comprising a stack including:
   a connecting conductor having conductive patterns; and
   a piezoelectric plate disposed on the connecting conductor, wherein
   the stack has first dividing slits at predetermined intervals, the first dividing slits dividing the stack into transducers separate from one another and arrayed in a scanning direction;
   the conductive patterns are electrically connected to the transducers;
   each of the transducers has a second dividing slit parallel to the first dividing slits, the second dividing slit dividing each of the transducers into subelements;
   the first dividing slits extend through the connecting conductor; and
   the second dividing slits are shallower than the first dividing slits and have bottoms apart from the connecting conductor.

2. The ultrasound probe according to claim 1, wherein a ratio of a depth of the first dividing slits to a depth of the second dividing slits is higher than 1.0 and not higher than 1.2.

3. The ultrasound probe according to claim 1, wherein a proportion of a depth of the second dividing slits to a thickness of the piezoelectric plate is not lower than 90% and lower than 100%.

4. An ultrasound probe comprising a stack including:
   a piezoelectric plate;
   a back reflecting layer disposed on a back surface of the piezoelectric plate; and
   a connecting conductor having conductive patterns, wherein
   the stack has first dividing slits at predetermined intervals, the first dividing slits dividing the stack into transducers separate from one another and arrayed in a scanning direction;
   the conductive patterns are electrically connected to the transducers;
   each of the transducers has a second dividing slit parallel to the first dividing slits, the second dividing slit dividing each of the transducers into subelements;
   the first dividing slits extend through the connecting conductor; and
   the second dividing slits are shallower than the first dividing slits and have bottoms apart from the connecting conductor.

5. The ultrasound probe according to claim 4, wherein the bottoms of the second dividing slits are located above an interface between the piezoelectric plate and the back reflecting layer.

6. The ultrasound probe according to claim 4, wherein a ratio of a depth of the first dividing slits to a depth of the second dividing slits is higher than 1.0 and not higher than 2.2.

7. The ultrasound probe according to claim 6, wherein the bottoms of the second dividing slits are located below a center in a thickness direction of the back reflecting layer.

8. An ultrasound diagnostic imaging apparatus comprising:
   the ultrasound probe according to claim 1, the ultrasound probe emitting ultrasound waves to a subject in response to a drive signal, and receiving ultrasound waves reflected by the subject to output a reception signal; and
   an image generation unit that generates ultrasound image data based on the reception signal outputted from the ultrasound probe.

9. An ultrasound diagnostic imaging apparatus comprising:
   the ultrasound probe according to claim 4, the ultrasound probe emitting ultrasound waves to a subject in response to a drive signal, and receiving ultrasound waves reflected by the subject to output a reception signal; and
   an image generation unit that generates ultrasound image data based on the reception signal outputted from the ultrasound probe.

* * * * *